(12) United States Patent
Xue

(10) Patent No.: US 9,883,835 B2
(45) Date of Patent: Feb. 6, 2018

(54) METHOD AND SYSTEM OF DIRECTING POSITIONING OF ECG ELECTRODES

(71) Applicant: General Electric Company, Schenectady, NY (US)

(72) Inventor: Joel Qiuzhen Xue, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 174 days.

(21) Appl. No.: 14/884,849

(22) Filed: Oct. 16, 2015

(65) Prior Publication Data

US 2017/0105678 A1 Apr. 20, 2017

(51) Int. Cl.
*G06K 9/00* (2006.01)
*A61B 5/00* (2006.01)
*H04N 13/02* (2006.01)
*A61B 5/0408* (2006.01)
*G06T 7/73* (2017.01)

(52) U.S. Cl.
CPC ............ *A61B 5/684* (2013.01); *A61B 5/0077* (2013.01); *A61B 5/0408* (2013.01); *G06T 7/73* (2017.01); *H04N 13/0203* (2013.01); *G06T 2207/10024* (2013.01); *G06T 2207/30048* (2013.01); *G06T 2207/30204* (2013.01)

(58) Field of Classification Search
None
See application file for complete search history.

(56) References Cited

U.S. PATENT DOCUMENTS

2014/0194760 A1\* 7/2014 Albert .................. A61B 5/0402 600/509
2017/0071492 A1\* 3/2017 van Dam ........... A61B 5/04012

\* cited by examiner

*Primary Examiner* — Atiba O Fitzpatrick
(74) *Attorney, Agent, or Firm* — Andrus Intellectual Property Law, LLP

(57) ABSTRACT

A method of directing positioning of ECG electrodes on a patient includes receiving at a processor an image of the patient with one or more electrodes and determining with the processor an actual location of each of the electrodes on the patient based on the image. The method further includes determining with the processor whether the actual location of each of the electrodes is correct and providing information via a user interface regarding the actual location of the electrodes.

21 Claims, 10 Drawing Sheets

METHOD AND SYSTEM OF DIRECTING POSITIONING OF ECG ELECTRODES

BACKGROUND

In electrocardiography, correct lead placement is very important and can greatly affect the waveforms obtained by an electrocardiograph (ECG) monitor. Accordingly, clinicians administering ECGs are often well trained on correct electrode placement. Moreover, there are a multitude of different electrode placement configurations which may be employed in various circumstances for obtaining ECGs, adding to the amount of training and expertise required in order to properly place electrodes for ECG monitoring.

Moreover, as regular ECG monitoring becomes an increasingly important part of healthcare, tools for providing and detecting proper electrode placement are becoming increasingly important and prevalent. Frequently, clinicians that are inexperienced in administering ECG tests are being called on to administer ECGs, including placing electrodes on patients. Additionally, home monitoring is becoming increasingly important, and thus patients are requiring guidance on how to place electrodes on themselves in order to administer their own ECGs.

As ECG electrode placement is such a technical and detailed practice, mistakes are commonly made in ECG electrode placement, leading to inaccuracies in ECG monitoring and waveform assessment. A multitude of tools have been developed attempting to determine whether improper electrode placement is causing inaccuracies in recorded ECG waveforms. Many of these tools assess the waveforms themselves in an attempt to assess and identify inaccurate lead placement. For example, multiple tools have been developed attempting to detect when electrodes are switched. However, these tools are generally ineffective at identifying problems with electrode placement and discerning the difference between abnormalities in waveforms caused by cardiac issues versus abnormalities resulting from incorrect electrode placement.

SUMMARY

The present invention alleviates problems recognized by the inventor regarding incorrect ECG electrode placement and prior art systems and methods attempting to detect and correct ECG electrode placement. This summary is provided to introduce a selection of concepts that are further described below in the Detailed Description. This summary is not intended to identify key or essential features of the claimed subject matter, nor is it intended to be used as an aid in limiting the scope of the claimed subject matter.

In one embodiment, a method of directing positioning of ECG electrodes on a patient includes receiving at a processor an image of the patient with one or more electrodes and determining with the processor an actual location of each of the electrodes on the patient based on the image. The method further includes determining with the processor whether the actual location of each of the electrodes is correct and providing information via a user interface regarding the actual location of the electrodes.

One embodiment of a system for directing positioning of electrodes on a patient includes a camera, one or more electrodes, and a positioning analysis module. The positioning analysis module is executable by a processor to receive an image taken with the camera of the patient's chest with the electrodes placed thereon. The positioning analysis module is further executable to determine an actual location of each of the electrodes based on the image, and to determine whether the actual location of each of the electrodes is correct. The positioning analysis module is further executable to provide information regarding the actual location of each of the electrodes.

One embodiment of a non-transitory computer readable medium has computer-executable instructions stored thereon, wherein the instructions include the steps comprising receiving a photograph of a patient with one or more electrodes, generating a representative image of the patient based on the photograph, and determining a desired location for each of the electrodes based on the image. The instructions further include the steps of determining an actual location for each of the electrodes based on the image, and determining whether the actual location for each of the electrodes is equivalent to the corresponding desired location. Further, the instructions include the steps of determining an adjustment instruction and providing the adjustment instruction to the patient.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

Figure 1A:
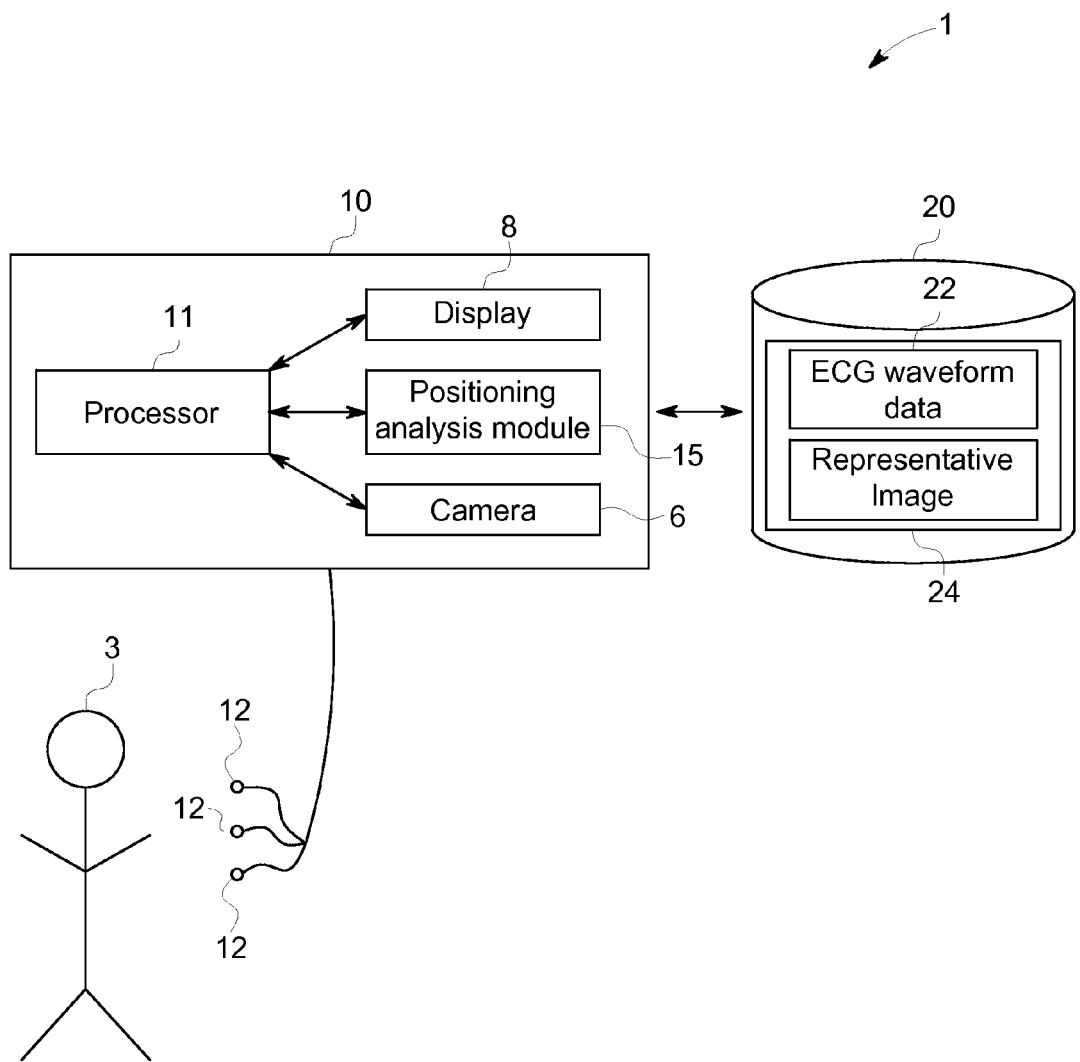
FIG. 1A depicts one embodiment of a system for directing positioning of ECG electrodes on a patient.
Figure 1B:
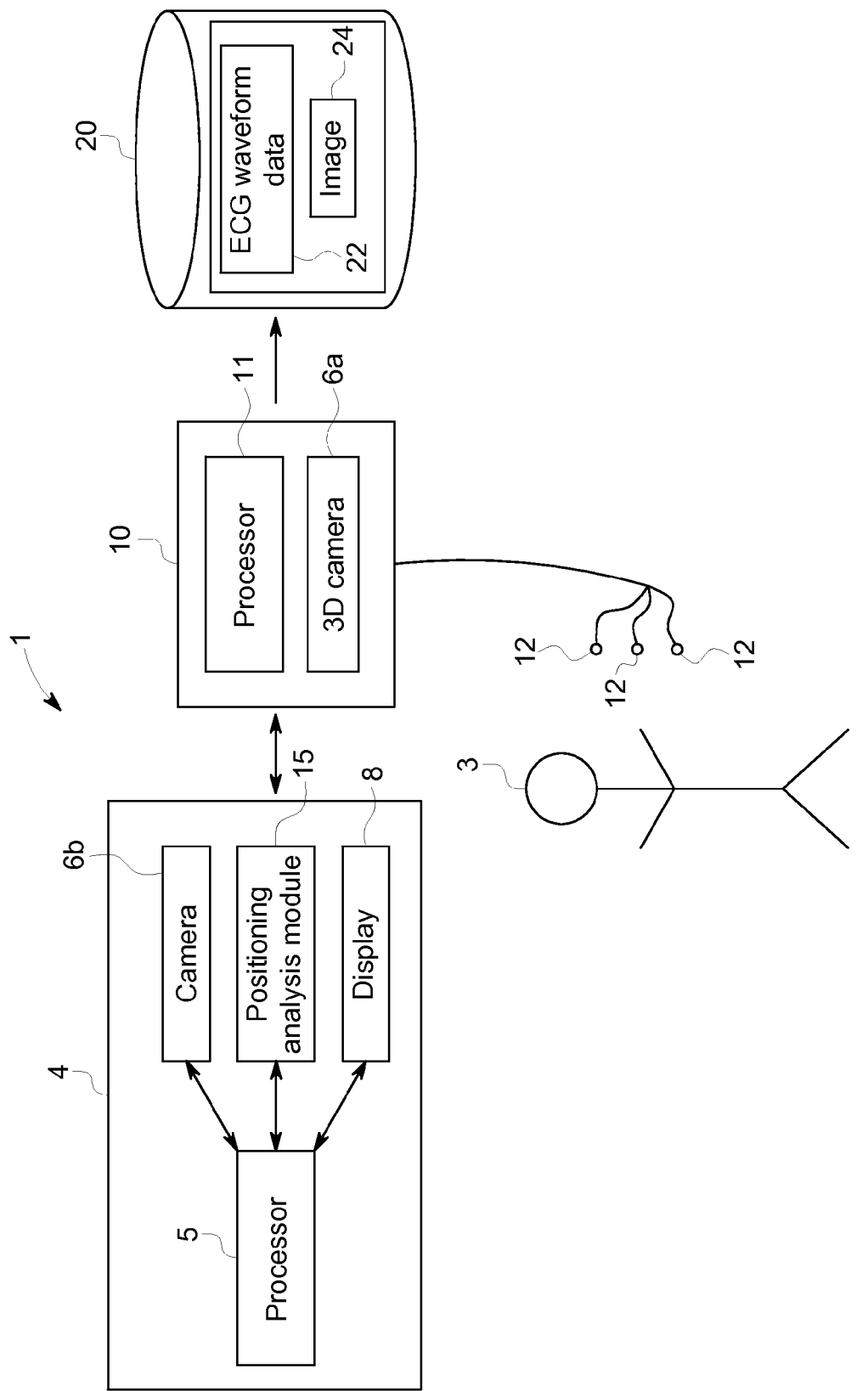
FIG. 1B depicts another embodiment of a system for directing position of ECG electrodes on a patient.
Figure 2:
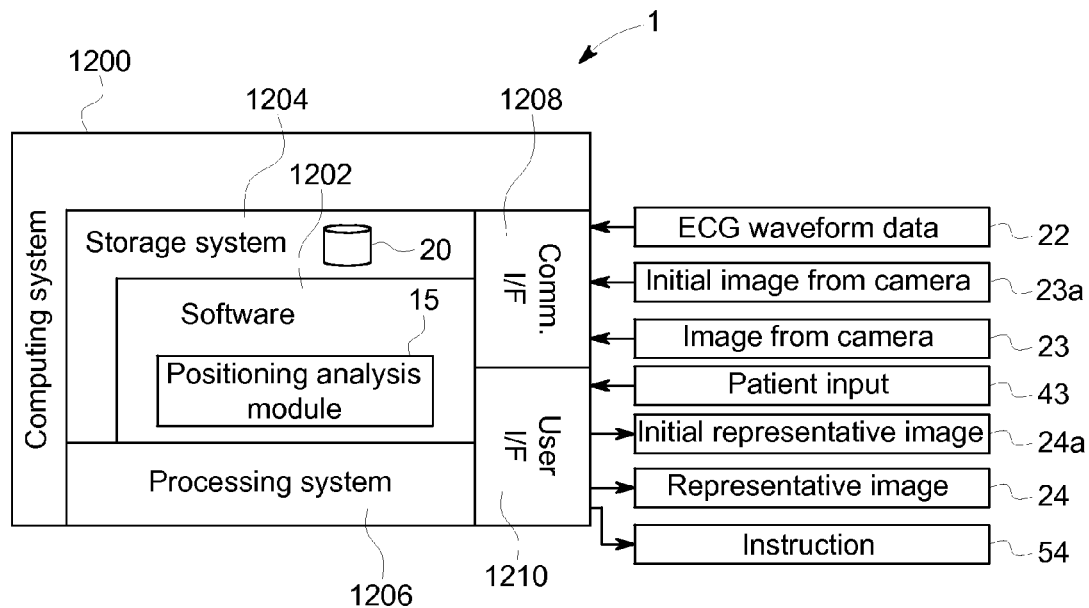
FIG. 2 depicts another embodiment of a system for directing position of ECG electrodes on a patient.

FIGS. 1A, 1B and 2 depict various embodiments of a system for directing positioning of ECG electrodes on a patient. In the embodiment of FIG. 1A, the system 1 for directing placement of ECG electrodes includes a patient monitor 10 connected to electrodes 12. For ease of depiction, three electrodes 12 are included in the figure; however, one of skill in the art will understand that any of various numbers of electrodes 12 may be utilized to obtain an ECG recording. In a common example, ten electrodes 12 are placed on the patient 3 in a standard 12-lead ECG arrangement. By way of example, FIG. 3B depicts an exemplary standard 12-lead ECG arrangement, which has six precordial electrodes (V1-V6) and four limb electrodes (RA, LA, RL, LL). Other ECG electrode and lead configurations are known in the art, including configurations using three, four, five, or six ECG electrodes.

In the embodiment of FIG. 1A, the ECG monitor 10 includes a processor 11 connected to display 8 and camera 6. Further, the processor 11 is configured to enable access and execution of the positioning analysis module 15. The system 1 also includes database 20 housing ECG waveform data 22 and a representative image, such as a 2D or 3D torso contour, such as an image 23 or representative image 24 of the chest of the patient 3 with the electrodes 12 positioned thereon. For example, the image 23 and/or representative image 24 may be stored with the ECG waveform data 22, such that the image 23 and/or representative image 24 depict the electrode 12 arrangement on the chest of the patient 3 that was used to record the ECG waveform data 22. The image 23 and/or representative image 24 may further be stored with the ECG waveform data 22 such that it is accessible by a clinician viewing the ECG waveform data 22 so that the clinician can view how the electrodes 12 were placed on the patient 3 when the ECG waveform data 22 was recorded. This may provide information to the clinician that may be valuable in correctly interpreting the data.

As is described in greater detail below, the camera 6 is used to capture an image 23 of the patient 3 with the electrodes 12 placed on the patient's chest. The positioning analysis module 15 is then executed on the processor 11 to analyze the image 23 captured by the camera 6 to determine whether the electrodes 12 are placed correctly. For example, the camera may be either 2D picture camera or 3D picture camera. A 3D camera is capable of capturing depth of the patient's torso and/or body, and the 3D image file can be viewed from different perspectives, which can be controlled by physicians or nurses to see the electrode position more clearly. The positioning analysis module 15 further directs the providing of information to the patient 3, and/or to a clinician administering an ECG on the patient 3, regarding the location of the electrodes 12. For example, the positioning analysis module 15 may display the image 23 and/or representative image 24 on the display 8 with instructions regarding adjustment of the location of one or more of the electrodes 12 on the patient's chest.

In the embodiment of the system 1 depicted in FIG. 1B, the system 1 further includes a personal computing device 4 having its own processor 5, camera 6b and display 8. The personal computing device 4 may be configured to store, access, and execute the positioning analysis module 15. For example, the personal computing device 4 may be a smartphone, tablet, or laptop, and the positioning analysis module 15 may be software stored thereon. In one specific example, the positioning analysis module 15 may be an application stored in memory on the personal computing device 4 and executable by the processor 5 of the personal computing device 4 to perform as described herein, including displaying instructions to the patient 3 on the display 8 regarding electrode positioning. In the embodiment of FIG. 1B, the personal computing device 4 is communicatively connected to the ECG monitor 10, and the ECG monitor 10 is communicatively connected to the database 20. The system 1 may be configured to utilize the camera 6a on the patient monitor 10 and/or the camera 6b on the personal computing device 4 to capture the one or more images 24 as described herein. In a preferred embodiment, the camera 6, 6a, 6b is a 3D camera capable of capturing a three-dimensional image of the patient 3. However, it is also contemplated that the camera 6, 6a, 6b may alternatively be a standard camera capturing two-dimensional images, or photographs, or a video camera, or an infrared imager or camera. Likewise, the camera 6b in the personal computing device 4 may be any type of camera, including a 3D camera, a standard 2D camera, a video camera, or an infrared camera or imager. For example, the camera 6b may be a 3D camera device that connects to personal computing devices 4, like smartphones or tablets, which are known and available in the art.

FIG. 2 depicts another embodiment of a system 1 for directing ECG electrode placement. FIG. 2 provides another system diagram of an exemplary embodiment of the system 1 for directing positioning of ECG electrodes including a positioning analysis module 15 executable to provide information regarding electrode positioning as described herein. The system 1 includes a computing system 1200 that includes a processing system 1206, storage system 1204, software 1202, communication interface 1208 and a user interface 1210. The processing system 1206 loads and executes software 1202 from the storage system 1204, including the positioning analysis module 15, which is an application within the software 1202. The positioning analysis module 15 includes computer-readable instructions that, when executed by the computing system 1 (including the processing system 1206), the positioning analysis module 15 directs the processing system 1206 to operate as described in herein in further detail, including to execute the steps of receiving an image 23 of the patient 3 from the camera 6, determining the actual location of each electrode 12 on the patient's chest, determining whether the actual location is correct, providing information to the patient regarding the actual locations of the electrodes, and storing the image(s) 24 of the patient's chest along with the ECG waveform data 41 in database 20.

Although the computing system 1200 as depicted in FIG. 2 includes one software 1202 encapsulating one positioning analysis module 15, it should be understood that one or more software elements having one or more modules may provide the same operation. Similarly, while description as provided herein refers to a computing system 1 and a processing system 1206, it is to be recognized that implementations of such systems can be performed using one or more processors, which may be communicatively connected, and such implementations are considered to be within the scope of the description.

The processing system 1206 comprises processor 11 and/or processor 5, which may be microprocessors and other circuitry that retrieves and executes software 1202 from storage system 1204. Processing system 1206 can be implemented within a single processing device but can also be distributed across multiple processing devices or sub-systems that cooperate in existing program instructions. Examples of processing system 1206 include general purpose central processing units, application-specific processors, and logic devices, as well as any other type of processing device, combinations of processing devices, or variations thereof.

The storage system 1204, which includes the database 20, can comprise any storage media, or group of storage media, readable by processing system 1206, and capable of storing software 1202. The storage system 1204 can include volatile and non-volatile, removable and non-removable media implemented in any method or technology for storage of information, such as computer-readable instructions, data structures, program modules, or other data. Storage system 1204 can be implemented as a single storage device but may also be implemented across multiple storage devices or sub-systems, which may be accessible to the processor(s) 5, 11. For example, the software 1202 may be stored on a separate storage device than the database 20. Storage system 1204 can further include additional elements, such a controller capable of communicating with the processing system 1206.

Examples of storage media include random access memory, read only memory, magnetic discs, optical discs, flash memory, virtual memory, and non-virtual memory, magnetic sets, magnetic tape, magnetic disc storage or other magnetic storage devices, or any other medium which can be used to storage the desired information and that may be accessed by an instruction execution system, as well as any combination or variation thereof, or any other type of storage medium. In some implementations, the store media can be a non-transitory storage media. In some implementations, at least a portion of the storage media may be transitory.

The user interface 1210 is configured to receive input 43 from a patient 3, and to generate one or more instructions 54 to the patient 3. User interface 1210 can include a mouse, a keyboard, a voice input device, a touch input device for receiving a gesture from a user, a motion input device for detecting non-touch gestures and other motions by a user, and other comparable input devices and associated processing elements capable of receiving user input from a user, such as a patient 3. Output devices such as a video display or graphical display can display instructions 54 and an interface further associated with embodiments of the system and method as disclosed herein. Speakers, printers, haptic devices and other types of output devices may also be included in the user interface 1210.

As described in further detail herein, the system 1 receives one or more images 23 from the camera 6, and may also receive the patient's ECG waveform data 22. The image may be, for example, an image file, such as in the .jpg, .gif, .tiff, .bmp formats, or similar, or a video file, such as .webm, .gif, .mov, .wmv, .webm, .mp4 formats, or similar. The patient's ECG waveform data 22 may be recorded by patient monitor 10 through electrodes 12, which may be in analog or digital form. In still further embodiments, the patient's ECG waveform data 26 may be a streaming analog input received in real time or near-real time by the system 1.

FIGS. 3A-3D depict exemplary representative images 24 of a patient 3 including a contour representation 31 generated from an image 23 taken by camera 6. The generation and use of a representative image 24 may replace the image 23 from the camera and may remove any information therefrom which could be used to identify the patient, such as the patient's face or unique identifiers, such as scars, birthmark's, etc. By removing any identifying information from the image 23, such as a photograph or video, and not storing the original image 23, the system 1 can insure patient privacy.

Figure 3A:
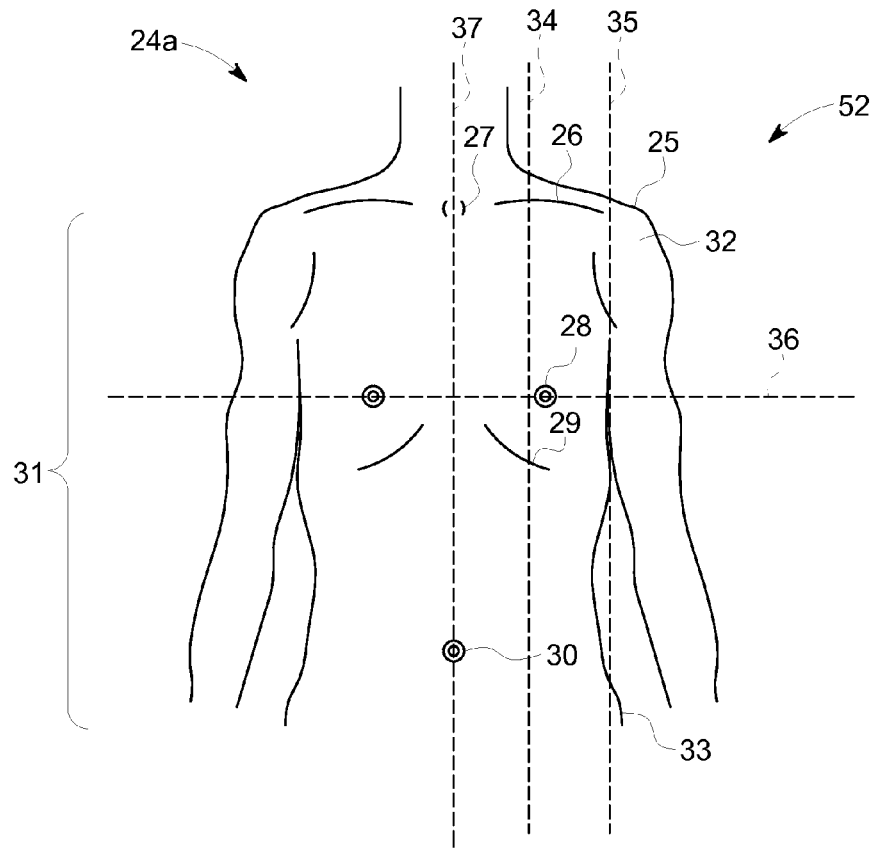
FIG. 3A depicts an exemplary representative image of a patient's chest.
Figure 3B:
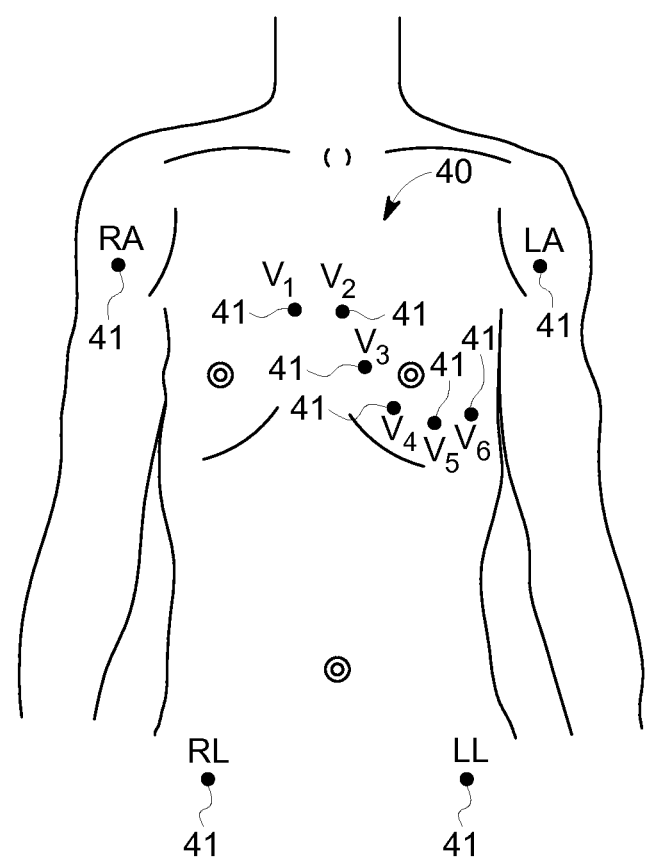
FIG. 3B depicts the exemplary representative image of FIG. 3A with desired electrode locations marked thereon.

In FIG. 3A, multiple anatomical markers 25-37 are located on the initial representative image 24a. The initial representative image 24a is generated from an initial image 23a taken with the camera 6 before electrodes are placed on the patient's chest. The purpose of the initial image 23a and/or the initial representative image 24a is to create an instruction mechanism to provide personalized information to the patient 3 (or the clinician, placing, the ECG electrodes 12 on the patient 3) regarding proper electrode 12 positioning. In other words, the initial image 23a and initial representative image 24a can be used to determine locations of desired locations 40 for electrodes 12, and to generate guidance to the patient in this respect.

The positioning analysis module 15 is configured to process the image 23 (such as the initial image 23a) from the camera 6 and/or the representative image 24 (such as the initial representative image 24a) in order to locate anatomical markers 52 such as those depicted in FIG. 3A, which include: the patient's right and left shoulder 25, clavicle 26, nipple 28, lower breast line 29, arm 32, and hip 33; as well as anatomical markers 52 along the mid-line of the patient, including the jugular notch 27 and navel 30. Further, anatomical markers 52 in the form of anatomical planes may be identified from the image, such as the vertical mid-line 37, mid-clavicular line 34, anterior axillary line 35, and chest line 36. Additionally, a contour 31 of the patient may be detected in the image 23 captured by camera 6 using known image processing algorithms such as edge detection, boundary extraction, and/or contour detection algorithms.

FIG. 3B depicts the initial representative image 24a with desired locations 40 marked for each of the ten electrodes 12 used in a standard 12-lead ECG. Markers 41, such as dots, are used to indicate the desired locations 40 of the precordial electrodes 12—including precordial electrodes V1, V2, V3, V4, V5, V6 and limb electrodes RA, LA, RL and LL. In one embodiment, the desired locations 40 of each electrode V1-V6, RA, LA, RL, and LL are determined based on the anatomical markers 52 and/or the contours 31 detected in the image 23 and/or the representative image 24. The location for correct electrode placement is typically defined in terms of anatomical markers 52 and, as such, the positioning analysis module 15 can be programmed to assess proper electrode placement for any number of electrode configurations based on the image 23 and/or representative image 24 of the patient.

In one embodiment the desired location markers 41 at the desired locations 40 may each be depicted in a unique, predetermined color that is the same color as the corresponding electrode that will be placed on the patient's 3 chest, either by the patient themselves or by a clinician. For example, the desired location markers 41 may follow the color coding used by the American Heart Association or by the International Electrotechnical Commission. The initial representative image 24a with the desired location markers 41 may then be displayed to the patient 3 (or to a clinician placing the electrodes 12 on the patient 3) to provide a guide, or example, of proper electrode 12 placement that is specifically tailored to the patient's body.

The patient may then place the one or more electrodes 12 following the color and placement of the desired location markers 41 depicted in the initial, representative image 24a. Likewise, the clinician may place the electrodes 12 on the patient 3 following the color and placement of the desired location markers 41 depicted in the initial representative image 24a. The patient 3 may then take another image 23 using the camera 6. A representative image 24 can then be generated from the image 24, according to the process explained above. In addition to the anatomical markers 52 and contour 31 detection, the positioning analysis module 15 may also locate the electrodes V1-V6, RA, LA, RL, and LL, in the image 23 and/or the representative image 24. For example, the positioning analysis module 15 may process the image 23 from the camera 6 or the representative image 24 to detect areas having the predefined colors and shapes of the various electrodes. The positioning analysis module 15 may then put actual location markers 47 corresponding to the actual locations V1-V6, RA, LA, RL, and LL detected on the image. Further, the actual location markers 47 may correspond in color and/or shape to the corresponding electrode. The actual locations 47 of the electrodes V1-V6, RA, LA, RL, and LL on the patient's chest are detected in the image 23 and actual location markers 49 are placed at the determined actual locations 47 on the representative image 24. As described above regarding determination of the desired locations 40, the actual locations 47 may be assessed based on their position relative to various anatomical markers 52, such as those depicted in FIG. 3A.

The actual location 47 for each of the electrodes V1-V6, RA, LA, RL, and LL are compared to the corresponding desired locations 40. For example, the actual locations 47 could be compared to the desired locations 40 based on the distance of each electrode location from one or more of the various anatomical markers 52. Alternatively or additionally, the actual locations 47 may be compared to the desired locations 40 by aligning and comparing the corresponding representative images 24 containing the respective markers 41, 49. In the context of the Figures, FIG. 3C could be aligned with and compared to FIG. 3B such that it could be determined whether the markers 49 for the actual locations 47 on the representative image 24 of FIG. 3C align with the markers 41 of the desired locations 40 on the initial representative image 24a of FIG. 3B. For example, the representative images 24 and 24a may be aligned according to the anatomical markers 52 and/or the contours 31 designated therein.

In addition to the location of the markers 41, 49 for the desired locations 40 and the actual locations 47, the images 23a and 23 and/or representative images 24a and 24 may be compared to assess whether the positions of any two or more electrodes are reversed, or transposed. Referring to FIG. 3D, while the actual locations 47 of each of the electrodes may reflect equivalent locations, or positions, compared to the desired locations 40, the electrodes V1 and V2 are transposed, with V1 on the left side of the patient and V2 on the right side of the patient. In order to detect this sort of error, the positioning analysis module 15 recognizes visual identifiers on each of the electrodes 12, such as V1-V6, RA, LA, RL, and LL. As described above, the visual identifiers may be, for example, color coding, such as according to national or international standards for ECG electrode color coding. In such an embodiment, the physical electrode 12 that the patient places on themselves or that the clinician places on the patient, will contain these visual identifiers, such as color coding, so that the positioning analysis module 15 can identify each electrode. Alternatively or additionally, the visual identifier may be an alphanumerical label, such as "V1," "V2," "V3," etc. Alternatively or additionally, each electrode 12, such as V1-V6, RA, LA, RL, and LL, may be illuminable, which may further assist the positioning analysis module 15 in identifying which electrode 12 is which. For example, each electrode 12 may have an LED therein that illuminates in the designated color, such as V1-red, V2-yellow, V3-green, etc. Further, the electrodes 12 may be separately illuminable by the positioning analysis module 15 such that the system could illuminate each electrode 12 in a pattern, which could be captured by the system and used to identify and verify the actual location 47 of each respective electrode. For example, the system 1 may be configured such that the camera 6 is configured to capture an image each time an electrode illuminates. In an embodiment where the camera 6 includes a video camera, the system 1 may operate such that the pattern of illumination of each electrode 12, such as V1-V6, RA, LA, RL, and LL, is captured on video. The enhanced color image can be analyzed by the positioning analysis module 15. The color shall match with the designed electrode labels, such as V1-red, V2-yellow, V3-green, etc.

Accordingly, the positioning analysis module 15 determines whether the actual locations 47 of each of the electrodes 12 is correct, and is equivalent to the desired locations 40. The equivalency determination may account for error in the image alignment, anatomical marker 52 and contour 31 detection, etc., and may also account for physical placement constraints based on the patient's physiology. For example, the desired locations 40 for each electrode may not be feasible based on the patient's physical features. For example, placement of the V3-V6 electrodes may be impeded by the presence of breast or adipose tissue on the patient's abdomen. Accordingly, based on the comparison between the actual locations 47 and the desired locations 40, and accounting for any equivalency factors, a determination is made regarding whether the actual locations 40 of each electrode 12 (such as V1-V6, RA, LA, RL, and LL) are correct. If the actual locations 47 are not correct, information may be provided to the patient or clinician regarding the actual locations 47 of the electrodes, such as whether the actual locations 47 are correct or incorrect and/or instructions for adjusting the actual locations 47.

In other embodiments, the initial imaging step may be eliminated and the positioning analysis module 15 may be configured to only receive an image 23 captured by camera 6 of the patient 3 with the one or more electrodes 12 already placed thereon. In such an embodiment, the positioning analysis module 15 may process the image 23 from the camera 6 and create a representative image 24 as described above. The positioning analysis module 15 then operates similarly to the above-described steps by determining the actual location 47 of each electrode and whether those actual locations 47 are correct. For example, the positioning analysis module 15 may identify anatomical markers 52 and/or contour representation 31, determine desired locations 40 for each electrode, and determine whether the actual locations 47 are equivalent to the desired locations. In such an embodiment where no initial image 23a is taken, the patient 3 and/or clinician may be presented with a generic image presenting a generic electrode configuration as guidance in making the initial electrode placement. In still other embodiments, the patient 3 and/or clinician may not need any initial guidance and may have enough familiarity with electrode placement in order to make an initial attempt at placing the electrodes. The system 1 can then be used to verify and correct that electrode placement.

Figure 3C:
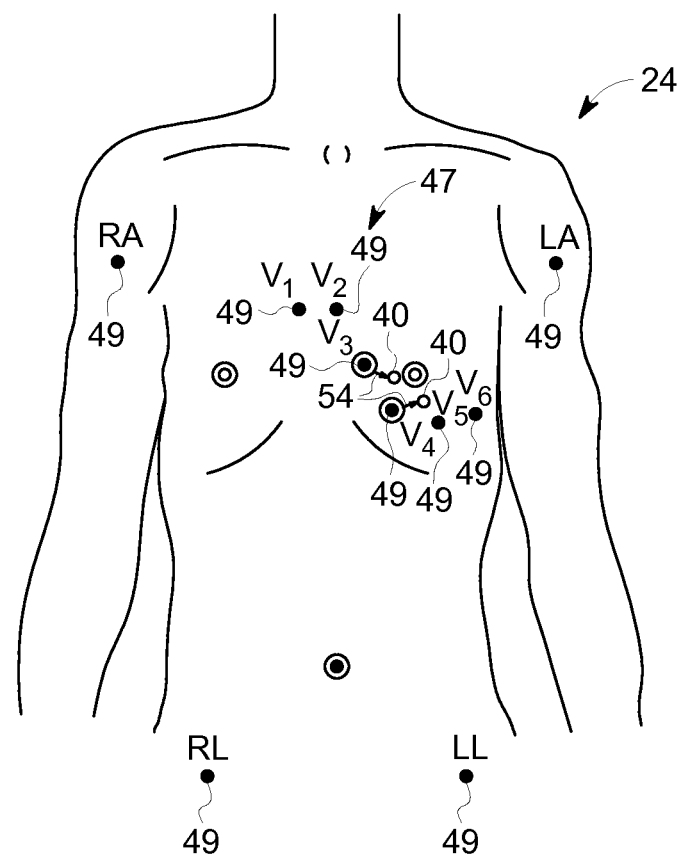
FIG. 3C depicts an exemplary representative image providing information regarding actual locations of electrodes and including adjustment instructions.
Figure 3D:
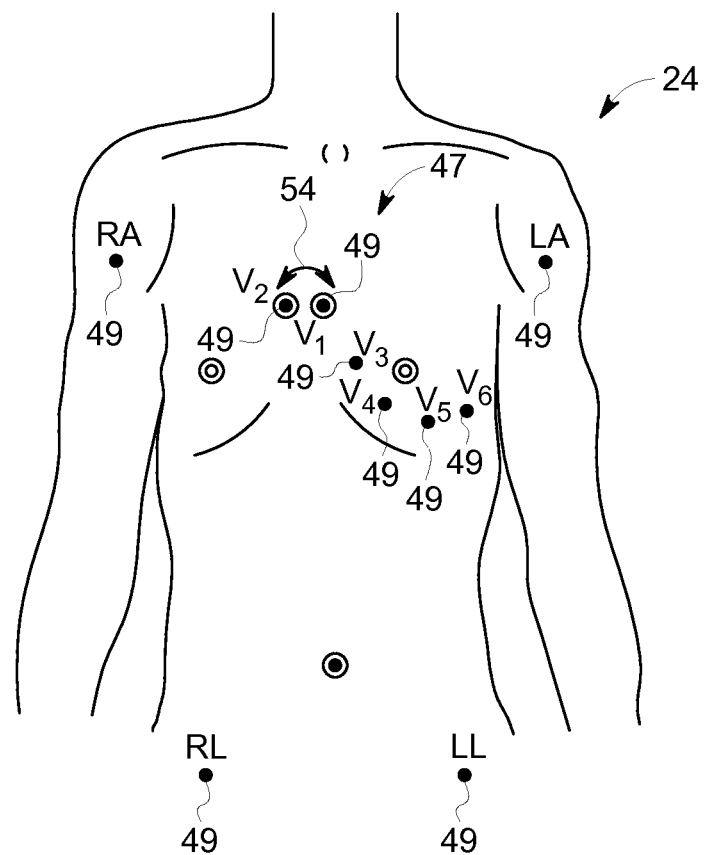
FIG. 3D depicts another embodiment of an exemplary representative image providing information regarding actual locations of electrodes and including adjustment instructions.

FIGS. 3C and 3D depict exemplary adjustment instructions 54 are illustrated on the representative images 24 conveying which electrodes need adjustment and what types of adjustments are required. In the exemplary FIG. 3C, for example, the positioning analysis module 15 has determined that the actual locations 47 of the V3 and V4 electrodes are not equivalent to the desired locations 40 for those electrodes. Adjustment instructions are generated and provided accordingly. The adjustment instructions 54 highlight the markers 49 for the actual locations 47 of the V3 and V4 electrodes and provide instruction on how to adjust the actual locations 47 of each electrode in order to align it with the corresponding desired locations 40. For example, the markers 49 for the actual locations 47 of misplaced electrodes may flash, pulse, or grow larger, in order to direct the patient's 3 or clinician's attention to the problem areas. Likewise, the same information may be conveyed by providing such indicators on the markers 41 for the desired locations 40 that are not properly achieved. Further, in embodiments where the electrodes are illuminable, the system 1 could illuminate the electrodes in need of adjustment. This could be done, for example, in conjunction with the adjustment instructions 54 presented on a display 8, such as those exemplified in FIGS. 3C and 3D.

In the exemplary FIG. 3D, the positioning analysis module 15 has determined that the V1 and V2 electrodes are reversed on the patient. Accordingly, the adjustment instructions 54 highlight the markers 49 for the actual locations 47 of the V1 and V2 electrodes and provide arrows indicating to the patient 3 and/or clinician to switch those two electrodes. In other embodiments, the adjustment instructions 54 may further include written or auditory instructions guiding the patient on adjustments that need to be made to the actual locations 47 of the electrodes.

In another embodiment, the electrodes 12 may be on an electrode strip or electrode harness, and the system may use the image 23 and/or the representative image 24 to determine whether the electrode strip or harness is properly placed. Similar assessment and instructions regarding placement of the strip or harness may then be provided to the patient.

Figure 4:
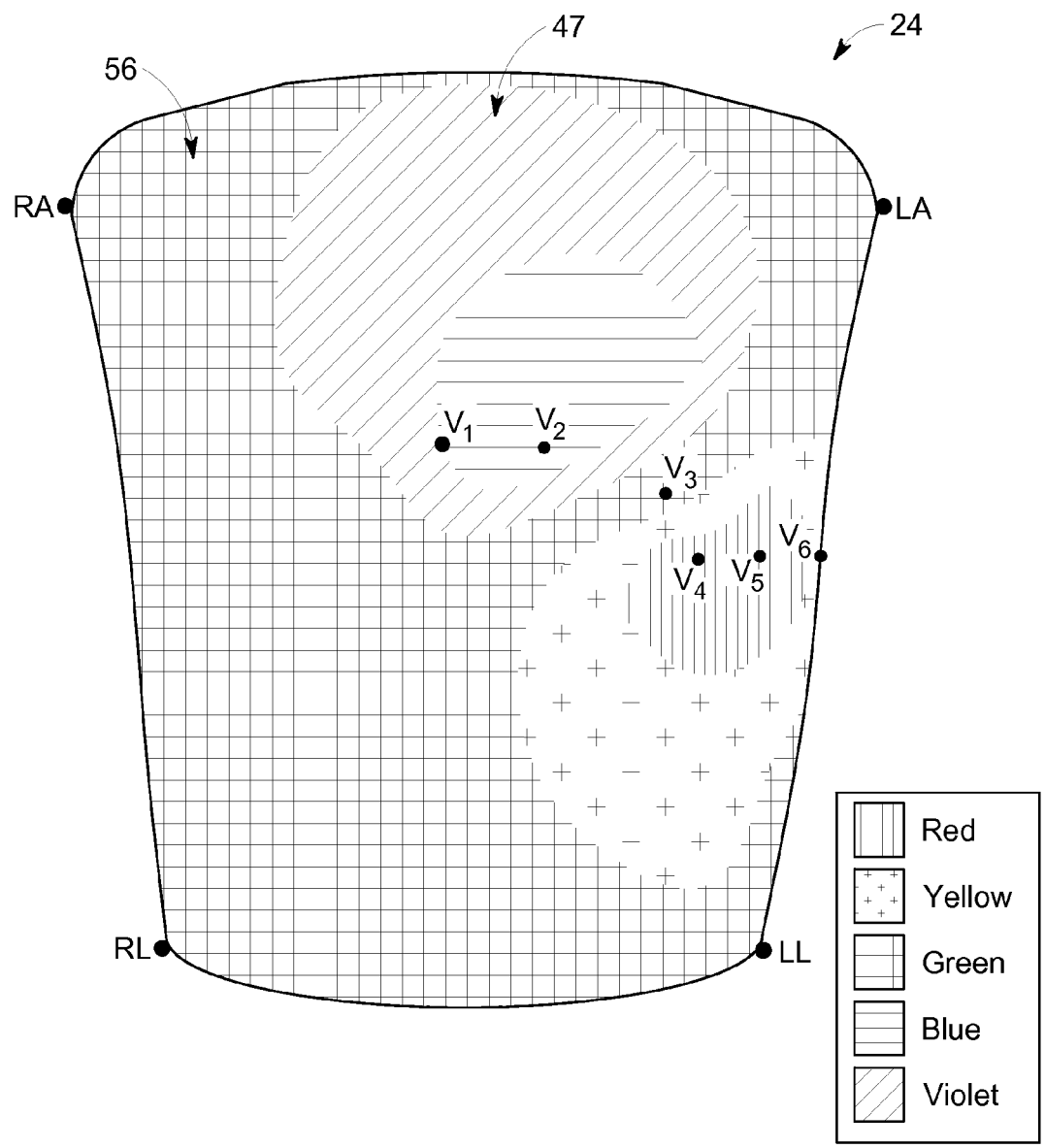
FIG. 4 depicts another embodiment of a representative image of a patient's chest having actual electrode locations marked thereon.

FIG. 4 depicts another embodiment of a representative image 24 with actual electrode locations 47 marked thereon. In the exemplary embodiment of FIG. 4, the representative image 24 is a color-coded map depicting the electric field distribution 56 in a patient's chest corresponding to the electrical activity generated by the patient's heart. The image is also called body surface potential map (BSPM). The various colors represented symbolically in FIG. 4 mark areas with relatively high and/or low electrical polarity during the patient's heart beat which can be used by the positioning analysis module 15 to determine the correct electrode placement. In the depicted embodiment, the color green depicts a relatively neutral, or zero, charge of most of the patient's chest. The colors red and yellow depict high, or positive, charges relative to neutral (with red being the highest), and the colors blue and violet depict low, or negative, charges relative to neutral (with violet being the most negative). Systems for detecting and mapping such electric field distribution 56 of a patient, including a patient's chest, are known in the art and BSPM is a known technique in the field of electrophysiology. A 3D torso with BSPM overlay can be very useful for identifying certain ECG abnormalities, like acute myocardial infarction and ischemia, where BSPM on the segment of ST shows a pattern of high contrast of 'red' and 'blue' regions or 'red' and 'green' regions. With the BSPM representative image 24 showing the actual electrode locations 47, a clinician can very quickly match the ST segment changes from a certain group of electrodes, and if the BSPM is showing true positive or false positive by matching the actual electrode locations with the correct electrode locations. In still other embodiments, maps similar to that depicted in FIG. 4 may be generated to depict heat distribution of the patient's chest. For example, such heat distribution of the patient's chest could be captured using thermal imagers, such as infrared camera systems, including 3D infrared cameras that capture 3-dimensional infrared images, a certain anatomical markers or physiological locations could be determined based thereon.

Figure 5:
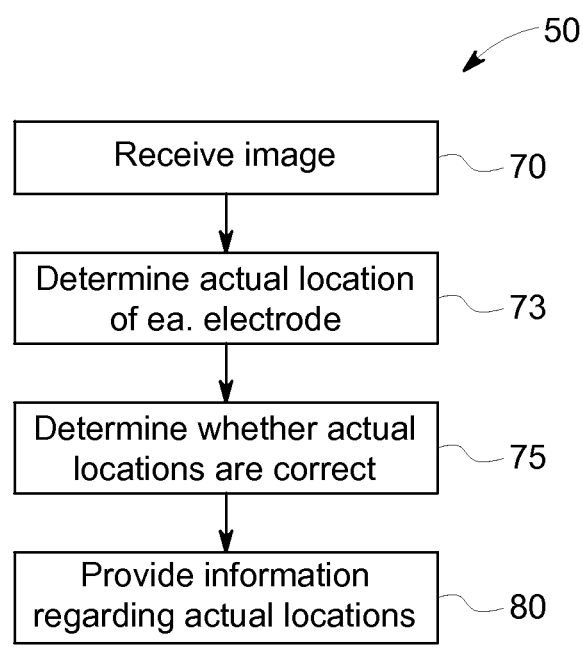
FIG. 5 depicts one embodiment of a method of directing electrode positioning.

FIG. 5 depicts one embodiment of a method 50 of directing electrode positioning. At step 70, an image is received, such as from a camera. An actual location of each electrode is determined at step 73 based on the received image. At step 75, it is determined whether the actual locations of each electrode are correct. Then, information is provided at step 80 regarding the actual locations.

Figure 6:
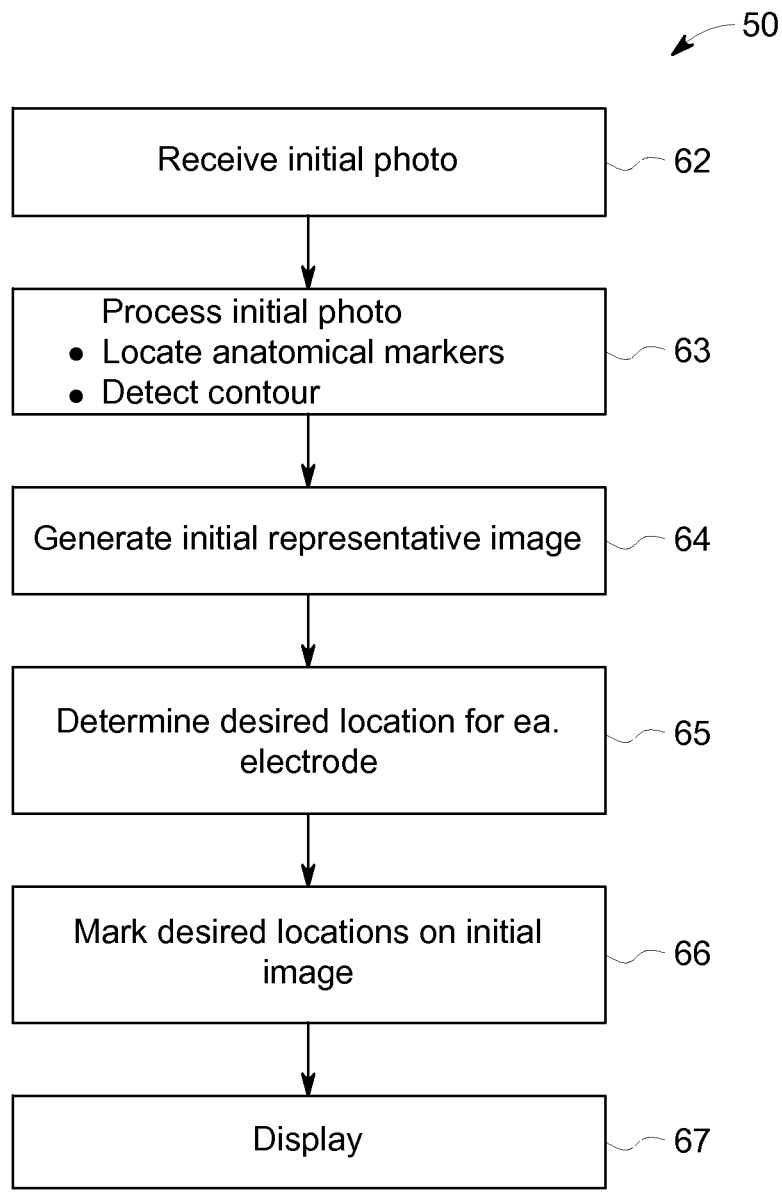
FIG. 6 depicts another embodiment of a method of directing electrode positioning.

FIG. 6 depicts another embodiment of a method 50 of directing electrode positioning. An initial image in the form of a photograph is received at step 62, such as from a camera. The initial image is then processed at step 63, such as to locate anatomical markers and/or detect contours of the patient's chest. Alternatively or additionally, step 63 may include detecting an electric field distribution and/or heat distribution of the patient's chest and determining markers used thereon. At step 64, an initial representative image is generated of the patient's chest. A desired location for each electrode is determined at step 65, and the desired locations for each electrode are marked on the initial image at step 66. At step 67, the initial image with desired location markings is displayed, such as on the user interface 1210 associated with the system 1.

Figure 7:
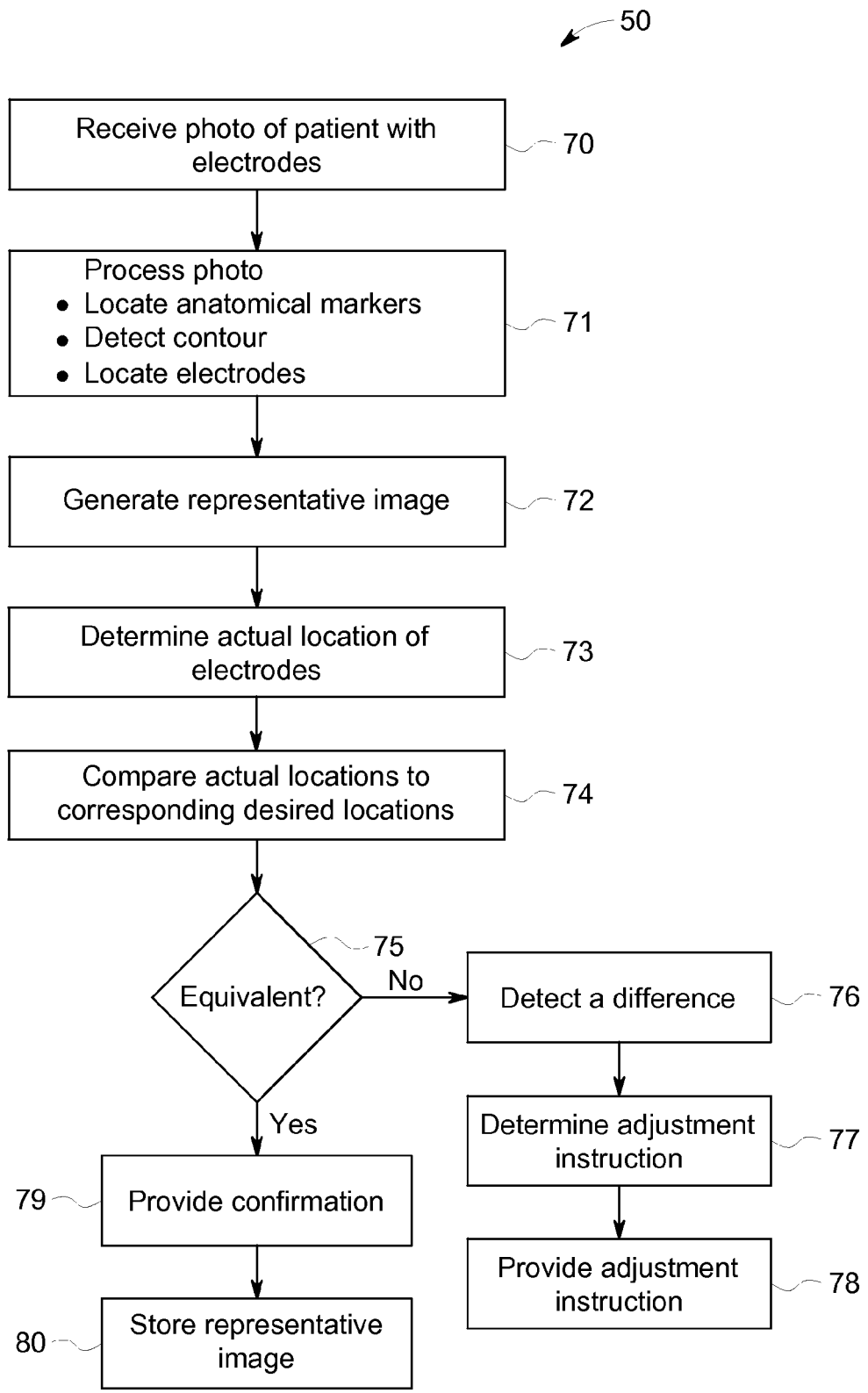
FIG. 7 depicts another embodiment of a method of directing electrode positioning.

FIG. 7 depicts another embodiment of a method 50 of directing positioning of ECG electrodes on a patient. The method 50 of FIG. 7 may be used alone or in conjunction with the method depicted in FIG. 6. At step 70, an image in the form of a photograph of a patient with the electrodes placed thereon is received. The photograph is processed at step 71, such as to locate anatomical markers, detect the contour of the patient's chest, and locate the electrodes. A representative image is generated at step 72. At step 73, an actual location of the electrodes is determined. Then, at step 74 the actual location of each electrode is compared to a corresponding desired location for that electrode. At step 75, it is determined whether the actual locations are equivalent to the corresponding desired locations, and thus whether the actual locations are correct. If equivalency is found at step 75, then the system continues to step 79 where confirmation is provided that the electrode placement is correct. At step 80, the image and/or the representative image with the actual location markings marked thereon may then be stored in the database along with the ECG waveform data recorded by the depicted electrode positioning.

If, on the other hand, one or more of the actual locations is not equivalent to the corresponding desired locations at step 75, then the system continues to step 76 where a difference is detected between those identified actual and desired locations. Based thereon, an adjustment instruction is determined at step 77; and then the adjustment instruction is provided at step 78, such as to the patient 3 or a clinician positioning the electrodes on the patient.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A method of directing positioning of ECG electrodes on a patient, the method comprising:
   receiving an image of the patient with one or more electrodes at a processor, wherein the image of the patient is one of a 2-dimensional photograph, a 3-dimensional photograph, a video, and an infrared image;
   determining with the processor an actual location of each of the electrodes on the patient based on the image;
   generating a representative image of the patient's chest from the image, wherein generating the representative image includes detecting an electric field distribution of the patient's chest within the image;

determining with the processor whether the actual location of each of the electrodes is correct based on the representative image; and providing information via a user interface regarding the actual location of the electrodes.

2. The method of claim 1, wherein the step of generating the representative image includes detecting a contour of the patient's chest within the image.

3. The method of claim 1, wherein the step of determining the actual location of each of the one or more electrodes on the patient includes determining the actual location of each of the one or more electrodes in the image with respect to the electric field distribution.

4. The method of claim 1, further comprising:
receiving an initial image of the patient at the processor;
processing with the processor the initial image to generate an initial representative image of the patient's chest;
marking desired locations of each of the one or more electrodes on the initial representative image with the processor; and
displaying the initial representative image with the desired location markings on the user interface.

5. The method of claim 4, wherein the step of determining whether the actual location of each of the electrodes is correct includes comparing the desired locations with the actual locations.

6. The method of claim 5, wherein the step of providing information on the actual location of the electrodes includes providing an adjustment instruction.

7. The method of claim 1, further comprising storing the image and/or the representative image in a database with ECG waveform data recorded from the one or more electrodes.

8. A system for directing positioning of ECG electrodes on a patient, the system comprising:
a camera;
one or more electrodes, each electrode having a visual identifier thereon that indicates an intended position for the electrode; and
a positioning analysis module executable by a processor to:
receive an image taken with the camera of the patient's chest with the electrodes placed thereon;
identify the visual identifier of each electrode;
determine an actual location of each of the electrodes based on the image and the visual identifier for each of the electrodes;
determine whether the actual location of each of the electrodes is correct; and
provide information regarding the actual location of each of the electrodes.

9. The system of claim 8, further comprising an ECG monitor having a processor configured to execute the positioning analysis module, wherein the camera is communicatively connected to the ECG monitor.

10. The system of claim 8, wherein the camera is a 3D camera and the image is a 3D image.

11. The system of claim 8, further comprising a personal computing device having a processor configured to execute the positioning analysis module, wherein the camera is communicatively connected to the personal computing device.

12. The system of claim 8, wherein the visual identifier is a predefined color for each intended position for the electrode.

13. The system of claim 8, wherein each of the electrodes is illuminable.

14. The system of claim 8, wherein the one or more electrodes are on an electrode strip or an electrode harness.

15. The method of claim 8, wherein the positioning analysis module is further executable by a processor to provide an adjustment instruction.

16. A non-transitory computer readable medium having computer-executable instructions stored thereon, wherein the instructions include the steps comprising:
receiving a photograph of a patient with one or more electrodes, each electrode in the image having a visual identifier thereon that indicates an intended position for the electrode;
generating a representative image of the patient based on the photograph;
determining a desired location for each of the electrodes based on the image;
identifying the visual identifier of each electrode;
determining an actual location for each of the electrodes based on the image and the visual identifier of each electrode;
determining whether the actual location for each of the electrodes is equivalent to the corresponding desired locations;
determining whether the actual location for each of the electrodes is equivalent to the intended location;
determining an adjustment instruction; and
providing the adjustment instruction.

17. The system of claim 8, wherein the a positioning analysis module is further executable by a processor to determine, based on the visual identifiers, whether one or more electrodes are in a correct order.

18. The system of claim 17, wherein the a positioning analysis module is further executable by a processor to determine, based on the visual identifiers, whether one or more electrodes are transposed.

19. The system of claim 8, wherein the visual identifier is an alphanumeric label.

20. The non-transitory computer readable medium of claim 16, wherein the step of determining whether the actual location for each of the electrodes is equivalent to the intended location includes determining, based on the visual identifiers, that one or more electrodes are transposed; and
wherein the step of the adjustment instruction is determined to instruct correction of the transposed electrodes.

21. The non-transitory computer readable medium of claim 16, wherein the visual identifier includes at least one of an alphanumeric label and a predefined color for each intended position for the electrode.

* * * * *